United States Patent
Chopra et al.

(10) Patent No.: US 6,408,678 B1
(45) Date of Patent: Jun. 25, 2002

(54) BURNISHING TAPE TESTING METHOD AND DEVICE

(75) Inventors: Manoj Chopra, Campbell; Charles H. Lee, San Jose, both of CA (US); Thorsten Lohmeyer, Woerrstadt (DE); Jay Allan Merz, Aromas; Hoa-Binh Tu, San Jose, both of CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/687,673

(22) Filed: Oct. 13, 2000

(51) Int. Cl.[7] ................................................. G01N 3/56
(52) U.S. Cl. ........................................ 73/9; 73/862.393
(58) Field of Search .............................. 73/9, 10, 826, 73/862.393

(56) References Cited

U.S. PATENT DOCUMENTS

| | | | |
|---|---|---|---|
| 3,872,629 A | 3/1975 | Malloy | 51/295 |
| 4,194,387 A * | 3/1980 | Hofbauer et al. | 73/9 |
| 5,176,028 A | 1/1993 | Humphrey | 73/150 |
| 5,355,636 A | 10/1994 | Harmon | 51/295 |
| 5,366,525 A | 11/1994 | Fujiyama | 51/295 |
| 5,404,751 A | 4/1995 | Beran et al. | 73/150 |
| 5,454,260 A | 10/1995 | Wang | 73/150 |
| 5,520,957 A | 5/1996 | Bange et al. | 427/208.8 |
| 5,546,797 A | 8/1996 | Dutta et al. | 73/150 |
| 5,673,586 A | 10/1997 | Mann | 73/150 |
| 6,283,838 B1 * | 9/2001 | Blake et al. | 451/63 |
| 6,290,573 B1 * | 9/2001 | Suzuki | 451/8 |

* cited by examiner

Primary Examiner—Max Noori
(74) Attorney, Agent, or Firm—Robert O. Guillot; Intellectual Property Law Offices

(57) ABSTRACT

The method for testing burnishing tape includes placing the tape on a backing surface and applying a force normal to the abrasive surface of the tape in a localized area of the tape surface. Thereafter, an increasing pulling force is applied to the end of the tape up to a point where the tape moves under the effect of the normal force. Through prior burnishing tape product testing a known normal force N is determined and a delamination pulling force D is likewise determined, such that a burnishing tape can be said to be defective where it is placed under a normal force N and the pulling force required to move it is less than the delamination pulling force D. The values of N and D are determinable for different types of burnishing tape and thereafter utilizable to test further quantities of similar burnishing tape.

The testing device of the present invention includes a tape supporting plate, a force gauge for applying a known normal force N to the abrasive surface of the burnishing tape disposed on the plate, and a variable torque motor with a torque sensor that is utilized to apply a known variable pulling force to the tape, such that the pulling force required to move the tape under the normal force N can be determined and then compared to the predetermined delamination force D. Where the pulling force required to move the tape is less than D the tape is determined to be defective, whereas when the pulling force required to move the tape is greater than D the bonding strength of the abrasive layer of the burnishing tape is determined to be adequate such that the burnishing tape can be confidently utilized to burnish hard disk surfaces.

8 Claims, 1 Drawing Sheet

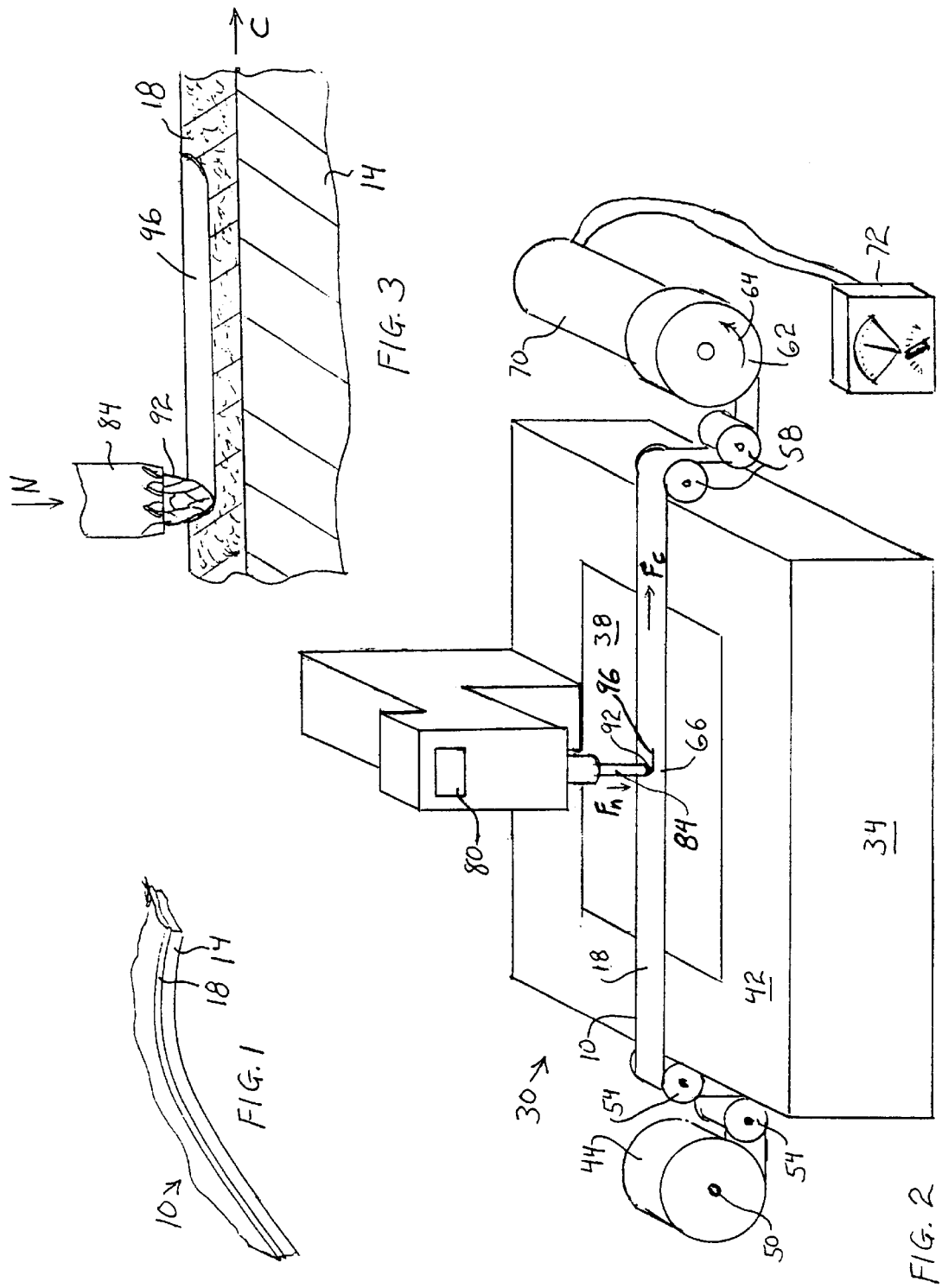

BURNISHING TAPE TESTING METHOD AND DEVICE

BACKGROUND OF THE INVENTION

1. Field of the Invention

The present invention relates generally to the testing of burnishing tape that is used in the fabrication of hard disks, and more particularly to methods and devices for testing the strength with which an abrasive material is bonded to the tape backing material of the burnishing tape.

2. Description of the Prior Art

Magnetic media hard disks generally include a wafer substrate having a magnetic media layer covered by a protective thin film surface layer including a diamond-like carbon (DLC) layer and a lubrication layer. A typical final step in the fabrication of such hard disks is a final burnishing of the disk surface to remove any projecting particulates and asperities from the surface of the disk, such that the finally fabricated disk has a smooth planar surface. This final burnishing step is a critical fabrication step in that the smoothness of the disk surface is a significant factor that affects the flying characteristics of a slider device which carries the read/write head of a hard disk drive. Thus, the performance of a hard disk drive is significantly influenced by the smoothness of the surfaces of its hard disks.

A typical burnishing process to which the present invention applies involves the utilization of a burnishing tape that includes a flexible backing material, such as Mylar, that has an abrasive material layer bonded to one surface. Generally, such burnishing tapes are manufactured utilizing large sheets of Mylar having smooth upper and lower surfaces. A slurry including a bonding agent and abrasive particles is applied to one surface of the Mylar sheet, and then dried and cured. Thereafter the Mylar sheet is cut into long, approximately one inch wide strips that are wound upon tape spools. One of the most significant process parameters of the burnishing tape is the bonding strength of the abrasive material layer to the Mylar tape surface. Where the bonding strength of the abrasive material to the Mylar surface is inadequate, abrasive particles can separate from the tape during the burnishing process, resulting in abrasive particulates being deposited upon the surface of the hard disks. Such delamination of the abrasive particles from the burnishing tape results in unacceptably high failure rates of hard disks, in that even a single abrasive particle resident upon the surface of a hard disk can cause a flying read/write head to crash, causing catastrophic damage to both the hard disk and the read/write head.

To solve the burnishing tape delamination problem, a method and device for testing the bonding strength of the abrasive material to the Mylar tape is required. The present invention provides such a burnishing tape testing method and device.

SUMMARY OF THE INVENTION

The method for testing burnishing tape includes placing the tape on a backing surface and applying a force normal to the abrasive surface of the tape in a localized area of the tape surface. Thereafter, an increasing pulling force is applied to the end of the tape up to a point where the tape moves under the effect of the normal force. Through prior burnishing tape product testing a known normal force N is determined and a delamination pulling force D is likewise determined, such that a burnishing tape can be said to be defective where it is placed under a normal force N and the pulling force required to move it is less than the delamination pulling force D. The values of N and D are determinable for different types of burnishing tape and thereafter utilizable to test further quantities of similar burnishing tape.

The testing device of the present invention includes a tape supporting plate, a force gauge for applying a known normal force N to the abrasive surface of the burnishing tape disposed on the plate, and a variable torque motor with a torque sensor that is utilized to apply a known variable pulling force to the tape, such that the pulling force required to move the tape under the normal force N can be determined and then compared to the predetermined delamination force D. Where the pulling force required to move the tape is less than D the tape is determined to be defective, whereas when the pulling force required to move the tape is greater than D the bonding strength of the abrasive layer of the burnishing tape is determined to be adequate such that the burnishing tape can be confidently utilized to burnish hard disk surfaces.

It is an advantage of the present invention that a method for testing burnishing tape has been developed.

It is another advantage of the present invention that a method for testing the bonding strength of the abrasive material layer of burnishing tape has been developed.

It is a further advantage of the tape burnishing test method of the present invention that the bonding strength of the abrasive layer of the burnishing tape can be measured.

It is yet another advantage of the burnishing tape testing method of the present invention that a determination can be made regarding whether abrasive particulates of the burnishing tape will delaminate from the burnishing tape during a hard disk burnishing process.

It is an advantage of the present invention that a device for testing burnishing tape has been developed.

It is another advantage of the present invention that a device for testing the bonding strength of the abrasive material layer of burnishing tape has been developed.

It is a further advantage of the burnishing tape testing device of the present invention that a roll of burnishing tape can be tested at several discrete locations throughout its length to generally determine the bonding strength of the abrasive material layer throughout the length of the tape.

These and other features and advantages of the present invention will no doubt become apparent to those skilled in the art upon reading the following detailed description which makes reference to the several figures of the drawings.

IN THE DRAWINGS

FIG. 1 is a cross-sectional view of a portion of a burnishing tape;

FIG. 2 is a perspective view of a burnishing tape testing device of the present invention; and FIG. 3 is an enlarged side cross-sectional view depicting the testing of a burnishing tape, wherein the burnishing tape is pulled beneath the diamond tip of the testing device depicted in FIG. 2.

DETAILED DESCRIPTION OF THE PREFERRED EMBODIMENTS

Burnishing tape is widely used in the hard disk drive industry to create a smooth outer surface on the hard disks, and a cross-sectional view of a portion of a typical burnishing tape 10 is provided in FIG. 1. The burnishing tape 10 includes a flexible backing material 14, such as Mylar, with an abrasive material layer 18 bonded to one surface of the Mylar backing material 14. As indicated above, if the abrasive material layer separates from the Mylar backing during the hard disk burnishing process, abrasive particulates may become resident upon the hard disk, and such hard disks are thereby rendered unusable. It has therefore become important to develop a burnishing tape testing method and device which can be utilized to test the burnishing tape prior to its use in fabricating hard disks.

A perspective view of the burnishing tape testing device 30 of the present invention is provided in FIG. 2. It is utilized to test the bonding strength of the abrasive material layer 18 to the Mylar backing 14 of the burnishing tape 10 that is depicted in FIG. 1. As depicted in FIG. 2, a test stand base 34 is provided having a generally rectangular smooth glass tape backing plate 38 disposed upon a top surface 42 thereof. A roll 44 of burnishing tape 10 is mounted upon a spindle 50 and the tape 10 is fed round tensioning rollers 54 and across the glass plate 38, and through further rollers 58 to a pickup reel 62. A calibrated torque motor 70 including a torque sensor with peak hold capabilities is engaged to the pickup reel 62 and utilized to rotate 64 the pickup reel 62. In a preferred control configuration, the torque sensor includes a calibrated electrical current metering device 72 that is utilized to control the current to the torque motor 70 which thereby controls the pulling force of the torque motor 70, such that a known pulling force can be applied from the pickup reel 62 to the tape 10. A portion 66 of the tape 10 is disposed upon the glass plate 38 with its abrasive side 18 upwards and its smooth side downwards against the glass plate 38. A calibrated (preferably digital) force gauge 80, including a downwardly depending stylus 84, is mounted above the glass plate 38, such that the stylus 84 is generally centrally located above the portion 66 of the burnishing tape on the glass plate 38. The stylus 84 preferably includes a diamond tip 92 for making contact with the abrasive surface 18 of the tape 66. The method of use of the testing device 30 is next described with aid of FIG. 3.

As indicated above, the bonding strength of the abrasive material layer 18 to the Mylar tape backing 14 is a critical process parameter of the burnishing tape 10. To obtain meaningful test data regarding the bonding strength of the abrasive layer 18, utilizing the testing device depicted in FIG. 2, a preload force is initially applied normal to the tape surface 18 utilizing the force gauge 80. That is, while the tape 10 is motionless, the diamond tip 92 is brought into contact with the abrasive surface 18 of the tape 66 against the glass plate, 38 and a known preload force $F_n$ is applied by the force gauge 80 through the diamond tip 92, normal to the abrasive surface 18 of the tape 66. Thereafter, utilizing the calibrated torque motor 70 on the pickup reel 62, a known pulling force is applied to the burnishing tape, starting with a zero pulling force. Initially, where a low pulling force is applied to the burnishing tape, it does not move owing to the frictional force created by the preloaded normal force $F_n$ of the diamond tip 92 against the tape 66. Thereafter, as the pulling force is increased, a point is reached at which the pulling force is greater than the frictional force, whereupon the tape portion 66 is pulled beneath the diamond tip 92, and an abraded line 96 is formed within the abrasive material layer 18 by the diamond tip. The pulling force that is required to overcome the frictional force created by the preloaded diamond tip is termed the critical force $F_c$ for purposes of this burnishing tape evaluation method.

An initial procedure in the utilization of the testing device of the present invention is to determine an appropriate value for the normal force $F_n$ that is initially applied to the tape. Basically, if the normal force is exceedingly low, such as 0.1 grams, the critical force would be quite low and no delamination of the abrasive material layer 18 from the Mylar backing 14 would occur, thus yielding no useful information about the bonding strength of the abrasive layer. Likewise, if an extremely large normal force, such as 1,000 grams, is applied to the tape, the critical force becomes exceedingly large, and the tape cannot be moved without destruction and delamination of the abrasive material layer 18 from the Mylar backing occurs in every test instance. However, it has been found that a useful range of normal force $F_n$ exists, wherein the critical force $F_c$ bears a strong relationship to the bonding strength of the abrasive material layer 18 to the Mylar backing. Specifically, through testing of a series of $F_n$ values, for a particular type of burnishing tape 10 as provided by a tape manufacturer, a predetermined normal force N can be determined and applied to the tape. Utilizing that normal force N, a critical delamination force D can then be determined which is related to the bonding strength of the abrasive material layer 18, such that the adhesive material delaminates from the tape at a pulling force D with a normal force N applied to the tape. Therefore, if the critical force $F_c$ of a specific portion of a test burnishing tape is less than D (where a normal force N is applied to the tape), it can be said that the bonding strength of the abrasive material layer 18 is too weak; such that the particular burnishing tape being tested is likely to delaminate during a hard disk burnishing step, and result in the deposition of abrasive particulates on the hard disk surface. In like manner, where a particular portion of a sample burnishing tape is tested with a normal force N in the test apparatus, and the critical force $F_c$ during the test is greater than D, it can be said that the bonding strength of the abrasive material layer 18 is strong enough that the burnishing tape being tested is not likely to delaminate during a subsequent disk burnishing process.

Therefore, in utilizing the test device and method of the present invention, it is first necessary to develop a predetermined normal force N that will be utilized in subsequent tape testing, as well as a predetermined delamination force D that will also be utilized in subsequent tape testing. The values of N and D can vary with regard to the nature of the tape backing, abrasive material bonding agents and other manufacturing parameters of the tape, as well as the hard disk burnishing equipment parameters. However, after the initial determination of N and D are made, such that burnishing tape which passes the test method does not delaminate during the hard disk burnishing step, subsequent burnishing tape of the that type can be effectively tested using the device and method of the present invention. In this test procedure to determine N and D, a tape specimen undergoes a series of tests utilizing predetermined normal force values such as 5, 10, 15, 20, 25, 30, 40 and 50 grams. With each normal force test, the critical force required to move the tape is determined and the abraded line 96 formed in each of the test tape specimens is examined using a magnifying glass or low power microscope to determine if delamination has occurred. Additionally, test hard disks are burnished with the tape and then examined to determine whether abrasive particulates have delaminated from the tape during the burnishing process. A plurality of burnishing tape specimens, including tape specimens that delaminated during hard disk burnishing and tape specimens that did not delaminate during hard disk burnishing are tested. Utilizing the test data, a normal force N is determined and correlated with a critical force $F_c$ at which a defective tape will become delaminated whereas a good tape will not become delaminated. This critical force is then selected as the delamination test force D. Thereafter, a normal force N can be applied to a tape specimen and the critical force $F_c$ for the tape specimen determined, and where the critical force $F_c$ is greater than D the tape is determined to be good, whereas where the critical force $F_c$ is less than D the tape is determined to be bad.

The present invention has been applied to burnishing tape manufactured by 3M Corporation, Minneapolis, Minn., having a Mylar backing and an abrasive slurry including alumina abrasive particulates having a diameter of approximately 0.1 to 1.0 microns and a polyester based bonding agent. The diamond tip of the stylus is rounded and has a diameter of approximately 0.1 microns. Where a predetermined normal force N of 20 grams was determined by initial testing and applied to the tape, a predetermined critical delamination force D of 140 grams was likewise determined. Using these parameters, burnishing tape rolls from a tape lot are selected from the beginning, middle and end of the lot. Each tape roll is tested in approximately six locations along its length and in each test sequence a normal force N of 20 grams is applied to the tape and the critical force $F_c$ is determined. The lot of burnishing tapes is deemed acceptable where the critical force $F_c$ from each individual test is greater than the predetermined delamination force D of 140 grams.

While the present invention has been shown and described with regard to certain preferred embodiments, it is to be understood that those skilled in the art will no doubt develop certain alterations and modifications in form and detail that nevertheless include the true spirit and scope of the invention. It is therefore intended that the following claims cover all such alterations and modifications that nevertheless include the true spirit and scope of the invention.

What is claimed is:

1. A method for testing burnishing tape comprising the steps of:

applying a normal force $F_n$ to an abrasive material surface of said burnishing tape;

applying a pulling force to said burnishing tape;

determining a critical pulling force $F_c$ at which said pulling force is sufficient to cause motion of said burnishing tape under the application of said normal force;

comparing said critical force $F_c$ with a predetermined force D, whereby if said critical force $F_c$ is less than said predetermined critical force D said tape is determined to be defective.

2. A method for testing burnishing tape as described in claim 1 wherein said predetermined force D is determined utilizing a predetermined normal force N, and said critical force $F_c$ is determined using a normal force $F_n$ that is equal to said predetermined normal force N.

3. A method for testing burnishing tape as described in claim 2 wherein said predetermined normal force N is applied to a predetermined area of said tape to be tested using a calibrated force gauge and a stylus.

4. A method for testing burnishing tape as described in claim 1 wherein said pulling force is applied to said tape utilizing a calibrated torque motor.

5. A method for testing burnishing tape as described in claim 1 wherein said predetermined normal force N is applied to said tape utilizing a diamond tipped force gauge.

6. A device for testing burnishing tape, comprising:

a means for applying a predetermined normal force N to an abrasive surface of a burnishing tape, wherein said means includes a force gauge;

a means for applying a calibrated variable pulling force to said tape, wherein said means includes a calibrated torque motor, and wherein said pulling force is sufficient to cause motion of said tape under the effect of said normal force.

7. A device for testing burnishing tape as described in claim 6 wherein said predetermined normal force N is approximately 20 grams.

8. A device for testing burnishing tape as described in claim 7 wherein said pulling force is approximately 140 grams.

* * * * *